US012495882B2

(12) United States Patent
Kantor

(10) Patent No.: US 12,495,882 B2
(45) Date of Patent: Dec. 16, 2025

(54) NON-INVASIVE DEVICE AND METHOD FOR FACE LIFT

(71) Applicant: Van J. Kantor, Tarzana, CA (US)

(72) Inventor: Van J. Kantor, Tarzana, CA (US)

( * ) Notice: Subject to any disclaimer, the term of this patent is extended or adjusted under 35 U.S.C. 154(b) by 1061 days.

(21) Appl. No.: 17/339,100

(22) Filed: Jun. 4, 2021

(65) Prior Publication Data

US 2022/0386761 A1 Dec. 8, 2022

(51) Int. Cl.
*A45D 44/22* (2006.01)
*A45D 44/00* (2006.01)
*A61F 5/08* (2006.01)

(52) U.S. Cl.
CPC .............. *A45D 44/22* (2013.01); *A45D 44/00* (2013.01); *A61F 5/08* (2013.01)

(58) Field of Classification Search
CPC ............ A45D 44/22; A45D 44/00; A61F 5/08
See application file for complete search history.

(56) References Cited

U.S. PATENT DOCUMENTS 1,195,117 A 8/1916 Spellerberg
2,001,862 A 5/1935 Battey
2,184,099 A 12/1939 Macdonald
2,896,613 A 7/1959 Brown
3,245,404 A 4/1966 Ritzcovan
3,782,372 A 1/1974 Carlton
4,499,896 A * 2/1985 Heinecke .......... A61F 13/00063 602/57
4,653,483 A 3/1987 Clavin
5,116,675 A 5/1992 Nash-Morgan
5,476,478 A 12/1995 Jackson
5,555,900 A 9/1996 Rich
5,582,585 A 12/1996 Nash-Morgan
5,755,232 A 5/1998 Kalt
5,890,486 A * 4/1999 Mitra ........................ A61F 5/08 606/204.45
5,957,126 A * 9/1999 Neeser ...................... A61F 5/08 606/204.45
6,045,470 A 4/2000 Wilcox et al.
6,065,470 A 5/2000 Van Cromvoirt et al.
6,769,429 B1 8/2004 Benetti
6,897,281 B2 5/2005 Lubnin et al.
7,067,710 B1 6/2006 Beaudry
(Continued)

FOREIGN PATENT DOCUMENTS

WO 03105585 12/2003

*Primary Examiner* — Jing Rui Ou
(74) *Attorney, Agent, or Firm* — Jordan IP Law, LLC

(57) ABSTRACT

A device and method for stretching skin of a user's face in a non-surgical, non-invasive manner is configured for adhesively attaching a first side surface of a first attachment portion of the device to one side of the user's face, pulling and stretching a central body portion of the device around a portion of a head of the user, during which a width of the central body portion narrows, and adhesively attaching a first side surface of a second attachment portion of the device to another side of the user's face. Prior to application, peelable cover pieces prevent undesired adhesive exposure and stretching of the central body portion. Upon application, the elasticity of the central body portion will cause pulling and smoothing of portions of the skin of the user's face. If desired, multiple devices can be employed simultaneously, potentially crisscrossing at a back head portion of the user.

19 Claims, 6 Drawing Sheets

(56) References Cited

U.S. PATENT DOCUMENTS

| | | | | |
|---|---|---|---|---|
| 7,473,158 | B2 | 1/2009 | Horton | |
| 7,608,090 | B2 | 10/2009 | Matsui | |
| 7,806,749 | B2 | 10/2010 | Horton | |
| 7,993,182 | B2 | 8/2011 | Horton et al. | |
| 8,062,329 | B2 | 11/2011 | Ierulli | |
| 10,603,221 | B1 * | 3/2020 | Kantor | A61F 13/128 |
| 2001/0032645 | A1 | 10/2001 | Cronk et al. | |
| 2002/0000227 | A1 | 1/2002 | Duyke et al. | |
| 2002/0029011 | A1 | 3/2002 | Dyer | |
| 2003/0232069 | A1 | 12/2003 | Horton | |
| 2005/0042264 | A1 | 2/2005 | Horton | |
| 2006/0115519 | A1 | 6/2006 | Matsui | |
| 2008/0097517 | A1 | 4/2008 | Holmes et al. | |
| 2008/0228217 | A1 | 9/2008 | Friend | |
| 2009/0076542 | A1 | 3/2009 | Jonn et al. | |
| 2009/0100558 | A1 | 4/2009 | Smith | |
| 2009/0111357 | A1 | 4/2009 | Horton | |
| 2009/0149114 | A1 | 6/2009 | Horton et al. | |
| 2014/0100599 | A1 | 4/2014 | Ha | |
| 2014/0243886 | A1 * | 8/2014 | Barian | A45D 44/22<br>606/204.35 |
| 2016/0015154 | A1 * | 1/2016 | Veeder | A45D 44/22<br>606/204.35 |
| 2016/0198835 | A1 * | 7/2016 | Iwagaki | A45D 44/22<br>428/41.8 |
| 2018/0027953 | A1 * | 2/2018 | Palmer | A45D 44/22 |

* cited by examiner

NON-INVASIVE DEVICE AND METHOD FOR FACE LIFT

BACKGROUND OF THE INVENTION

Field of the Invention

The present invention relates to a device and a method for providing a skin lift and, more particularly, a lift of excess skin across portions of the face of an individual.

Description of the Related Art

For decades, women and men have tried to look younger using cosmetic surgery to get rid of or minimize wrinkles, folds and excess skin. Surgeons cut the skin and lift it, and remove excess skin. This process of course has all the risks of any surgery. Moreover, it requires time for doctor's appointments, the procedure itself, and recuperation time, as well as being costly.

There have been many attempts to improve looks without surgery. For example, U.S. Pat. Nos. 5,116,675 and 5,582,585 to Nash-Morgan disclose devices that are elastic and adhere to the neck to help lift the skin on the front of the neck. However, these products are somewhat cumbersome to manufacture, involve the assembly of multiple different parts, and are consider uncomfortable and/or relatively non-effective. In addition, these know devices are not specifically designed for lifting the skin of the face of a person. Accordingly, a simpler, easier, more comfortable device dedicated to addressing face wrinkles is desirable.

SUMMARY OF THE INVENTION

The present invention is directed to a device and method for stretching skin of a user's face in a non-surgical, non-invasive manner. The device includes: a flexible and stretchable central body portion, a first attachment portion extending from a first end portion of the central body portion, and a second attachment portion extending from a second end portion of the central body portion. A first adhesion layer is provided on a first side surface of the first attachment portion and a similar, second adhesion layer is provided on a corresponding first side surface of the second attachment portion.

During use, the device is applied by first adhesively attaching the first side surface of the first attachment portion of the device to one side of the user's face, forward of a respective ear of the user. While pressing against the first attachment portion, the central body portion is pulled and stretched around a portion of the head of the user, during which a width of the central body portion narrows and a length thereof becomes elongated. After the central body portion reaches around the user's head, the first side surface of the second attachment portion of the device is adhesively attached to the other side of the user's head, such as the face or neck. Once fully attached, the elasticity of the central body portion will cause pulling and smoothing of portions of the skin of the user's face. If the user has sufficient hair to pull up prior to attaching the device, the device can be completely concealed after the hair is lowered.

For packaging and prior to use, a first peelable cover member is removably provided on the first adhesion layer, while a second peelable cover member is removably provided on the second adhesion layer. In addition, a peelable cover strip is provided along an opposing side of the central body portion, with the cover strip also preferably extending across second side portions of each of the first and second attachment portions. These covers prevent unintentional contact with the adhesive, while advantageously preventing stretching or other deformation of the central body portion, prior to use.

Additional objects, features and advantages of the present invention will become more readily apparent from the following detailed description of preferred embodiments when taken in conjunction with the drawings wherein like reference numerals refer to corresponding parts in the several views.

DETAILED DESCRIPTION OF PREFERRED EMBODIMENTS

Figure 1:
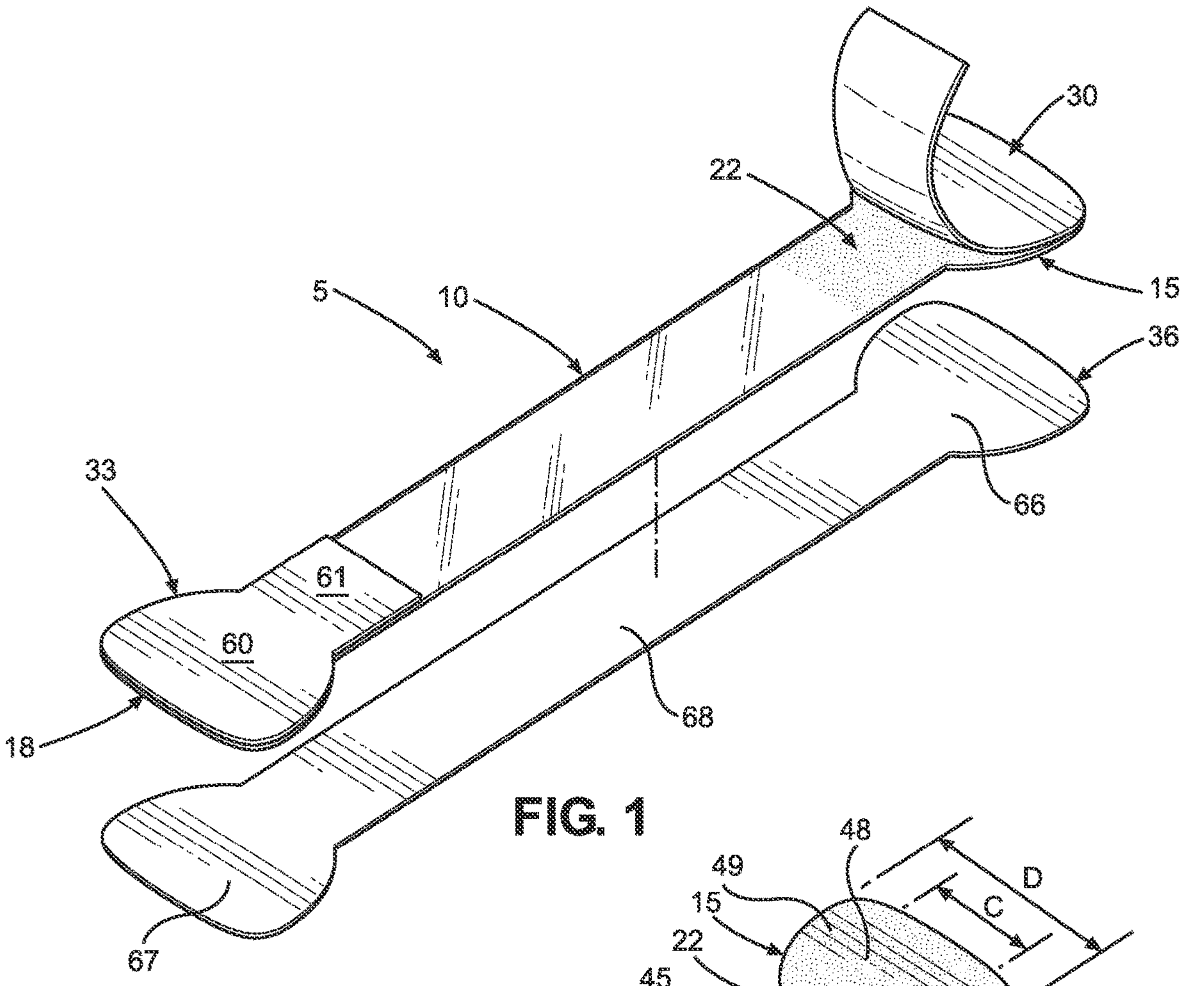
FIG. 1 is a perspective view of a device constructed in accordance with the present invention for stretching the skin of a user's face, with the device being shown in a partially exploded view.
Figure 2:
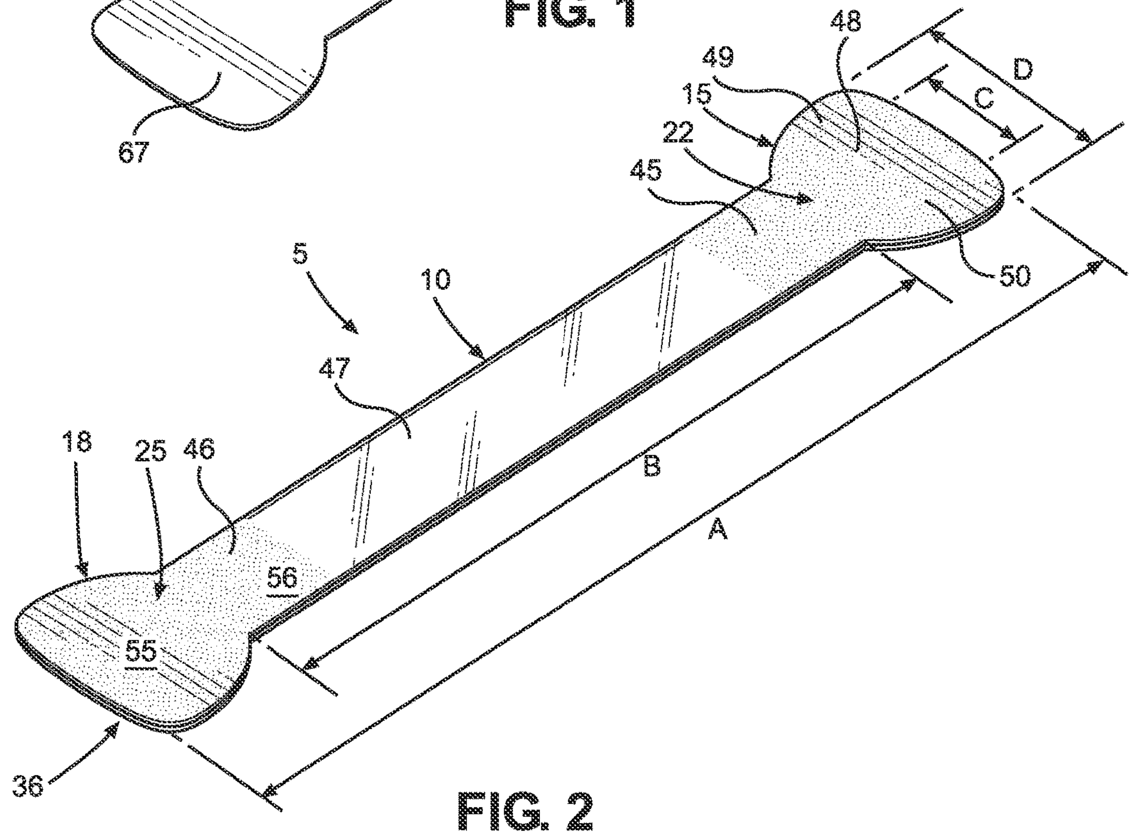
FIG. 2 is another perspective view of the device of FIG. 1.

With initial reference to FIGS. 1 and 2, a device for stretching the skin of a user's face in a non-surgical, non-invasive manner in accordance with the present invention is generally indicated at 5. As shown, device 5 includes a central body portion 10, a first attachment portion 15 and a second attachment portion 18. Although other materials and constructions are possible, at least central body portion 10 is made of stretchable material. Actually, central body portion 10, first attachment portion 15 and second attachment portion 18 of device 5 are preferably made as a single, integral piece from urethane as will be detailed more fully below.

Although not separately labeled, central body portion 10 has first and second opposing sides or faces. In a similar manner, each of first and second attachment portions 15 and 18 have respective first and second opposing side surfaces (not labeled). On the first side surface of first attachment portion 15 is provided a first adhesive layer 22. In a similar manner, the first side surface of second attachment portion 18 is provided a second adhesive layer 25. As shown in each of these figures, provided over first adhesive layer 15 is a first peelable cover member 30. In a corresponding manner, a second peelable cover member 33 is provided atop second adhesive layer 25. In addition to first and second peelable cover members 30 and 33, both of which are provided on the same side surface of device 5, a cover strip 36 is shown to extend along an entire length of an opposing side of device 5. First cover member 30, second cover member 33 and cover strip 36 are preferably formed from a non-sticky material, such as a plastics coated paper material, for purposes which will become evident from the discussion below.

Central body portion 10 of device 5 includes a first end portion 45, a second end portion 46 and a connecting portion 47. Although not mandated, first adhesive layer 22 extends into first end portion 45, while second adhesive layer 25 extends into second end portion 46. However, there is no adhesive employed along a majority of central body portion 10, particularly in connecting portion 47. As shown, first attachment portion 15 and second attachment portion 18 extend directly from first and second end portions 45 and 46, respectively, and are wider than central body portion 10 as each includes a central section 48, having a width commensurate with that of central body portion 10, and flared side sections 49 and 50.

With the above in mind and specific reference to FIG. 2, device 5 therefore has an overall length A, a central body length B, a central body width C, and an enlarged width D for first and second attachment portions 15 and 18. Although different dimensions could be employed to accommodate varying sized human heads, with or without hair, device 5, in particularly preferred forms, has an overall, pre-stretched length A generally between 6-9 inches, a central body length of approximately 4-7 inches, a central body width of ½-1 inch, and an enlarged width of about 1-1¾ inches. Not taking into account thicknesses for first and second adhesive layers 22 and 25, first and second cover members 30 and 33, or cover strip 36, device 5 preferably has a substantially uniform thickness along its entire length, such as in the adjustable range of approximately 0.5 to 2 millimeters thick.

As clearly shown in FIGS. 1 and 2, each of first and second adhesive layers 22, 25 includes a main section 35 covering the one side of a respective attachment portion 15, 18. Although not required, adhesive layers 22 and 25 also preferably extend into first and second end portions 45 and 46 of central body portion 10. In such embodiments as shown, each of first and second cover members 30, 33 includes both an attachment cover section 60 and a tab portion 61 extending into central body portion 10 to selectively cover the adhesive in a respective one of first and second end portions 45, 46. As indicated above, cover strip 36 preferably extends the entire length of device 5 on a side opposite the adhesive and cover members 30 and 33. Therefore, cover strip 36 includes a first end 66 located at first attachment portion 15, a second end 67 at second attachment portion 18 and a connecting portion 68 extending along central body portion 10. Like cover members 30 and 33, cover strip 36 is not sticky and is selectively peelable from a remainder of device 5. As indicated above, central body portion 10 is stretchable, while having a degree of elasticity. For this reason, cover strip 36 is preferably provided to establish predetermined and non-fluctuating length and shape characteristics for device 5 during packaging, shipping, storing, etc., basically until actual use which will now be set forth in detail with particular reference to FIG. 3-5 in describing the method of employing device 5 to stretch skin of a user's face.

Figure 4:
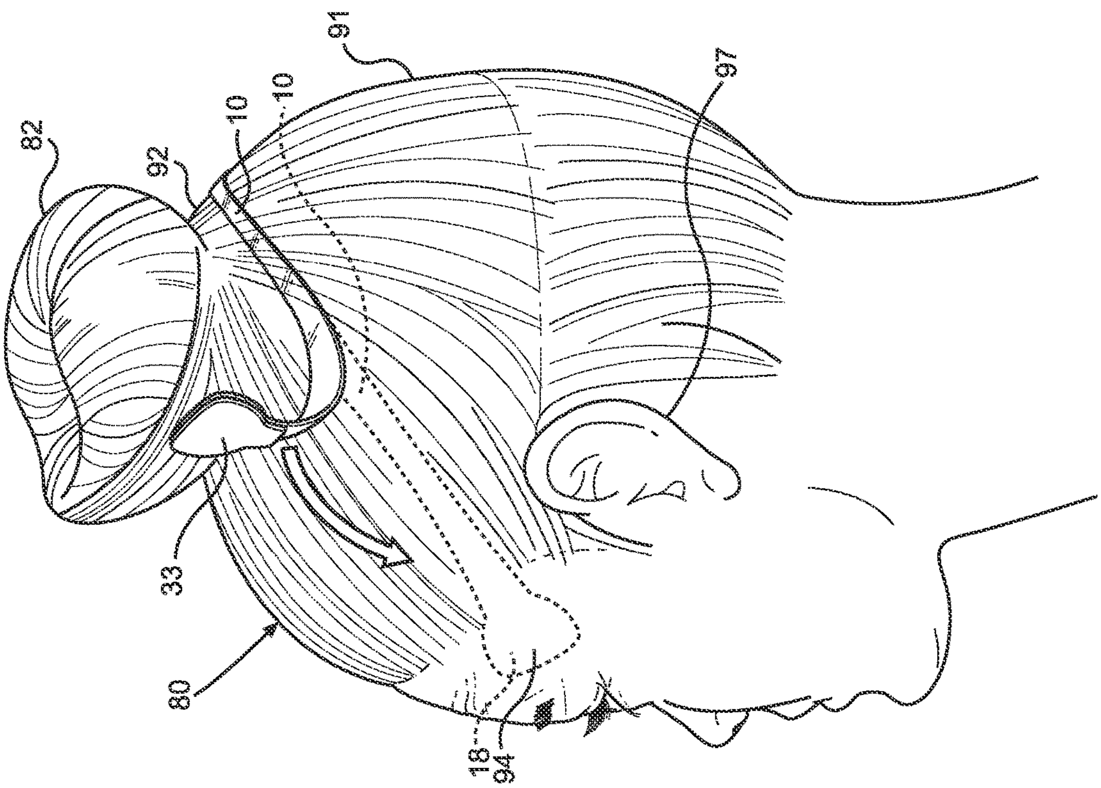
FIG. 4 shows latter stages in the method of FIG. 3.
Figure 3:
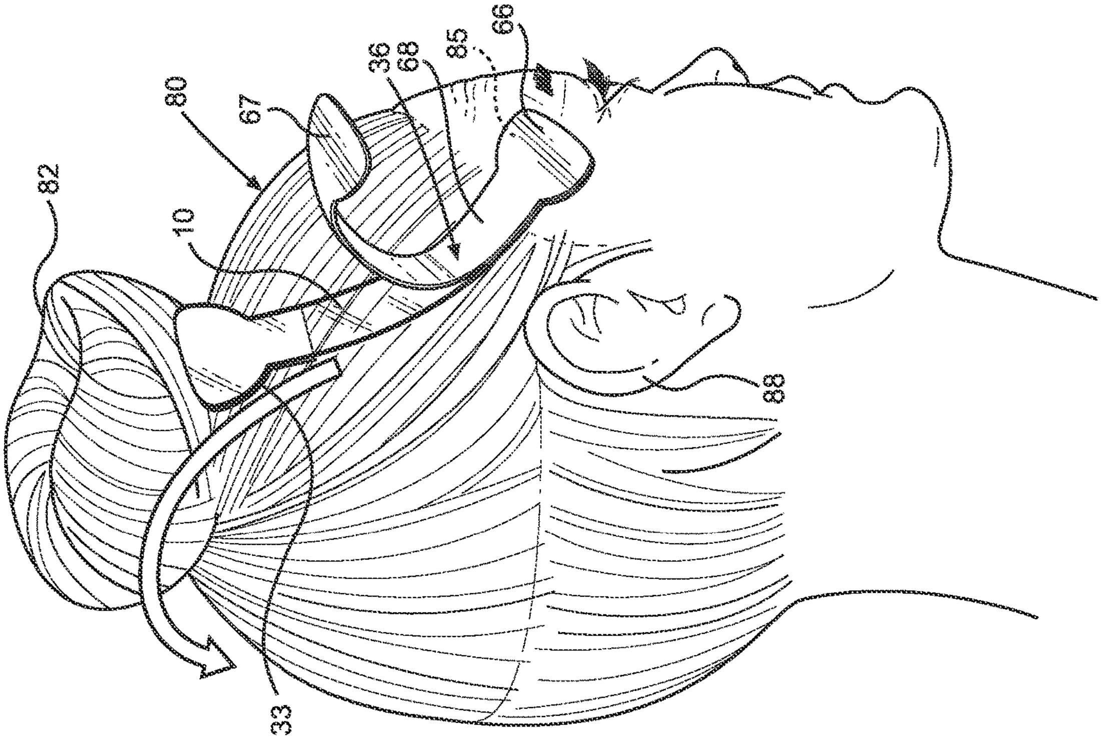
FIG. 3 illustrates an initial step associated with a method of non-invasively stretching the skin of a user's face with the device of FIGS. 1 and 2 in accordance with one preferred embodiment of the invention.
Figure 5:
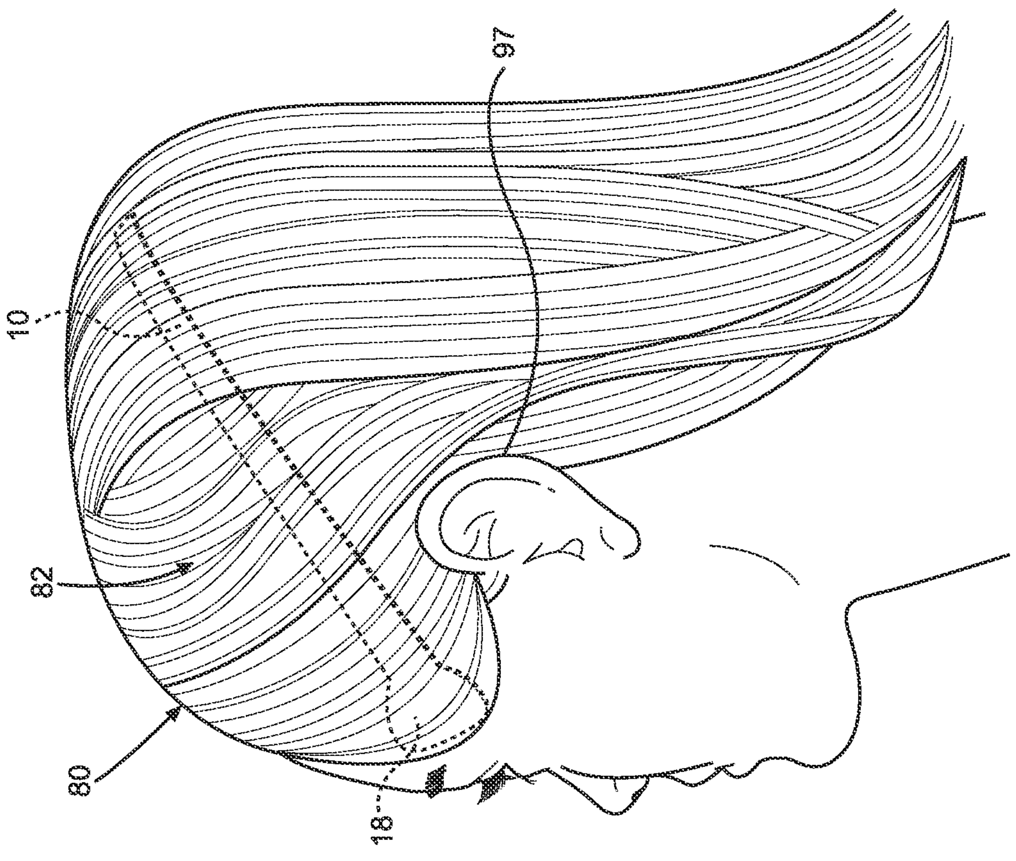
FIG. 5 shows a woman wearing the device of the present invention beneath her hair to stretch skin portions of her face in accordance with the method of FIGS. 3 and 4.

As shown best in FIG. 3, the head 80 of a user is shown with hair pulled up at 82. First cover member 30 has already been peeled to expose first adhesive layer 22 and first attachment portion 15 has been secured at a first attachment position 85 which is basically shown to be located near a temple portion of a user but, most importantly, is forward of a right ear 88. In a next stage of the method, cover strip 36 is completely removed. While pressing upon first attachment portion 15 and grasping second attachment portion 18 having second cover member 33, device 5 is pulled so that central body portion 10 is stretched across the back 91 and/or top 92 of head 80 as best shown in FIG. 4. When fully extended, second attachment portion 18 will reach a second attachment position 94 forward of left ear 97 (generally directly opposite and at a corresponding height to first attachment portion 15). Here, second cover member 33 is peeled to expose second adhesive layer 25 and second attachment portion 18 is adhered at second attachment position 94 as indicated with the use of the dotted lines in FIG. 4. Due to the elastic nature of device 5 (overall an elastic or resilient material that is skin-compatible) and particularly the elasticity of central body portion 10, attaching device 5 in this manner will cause pulling and smoothing of portions of the skin of the user's face. At this point, the hair 82 which was originally pulled up at the top 92 of head 80 can be let down to completely cover device 5 as clearly shown in FIG. 5 to finalize the attachment process.

Figure 6:
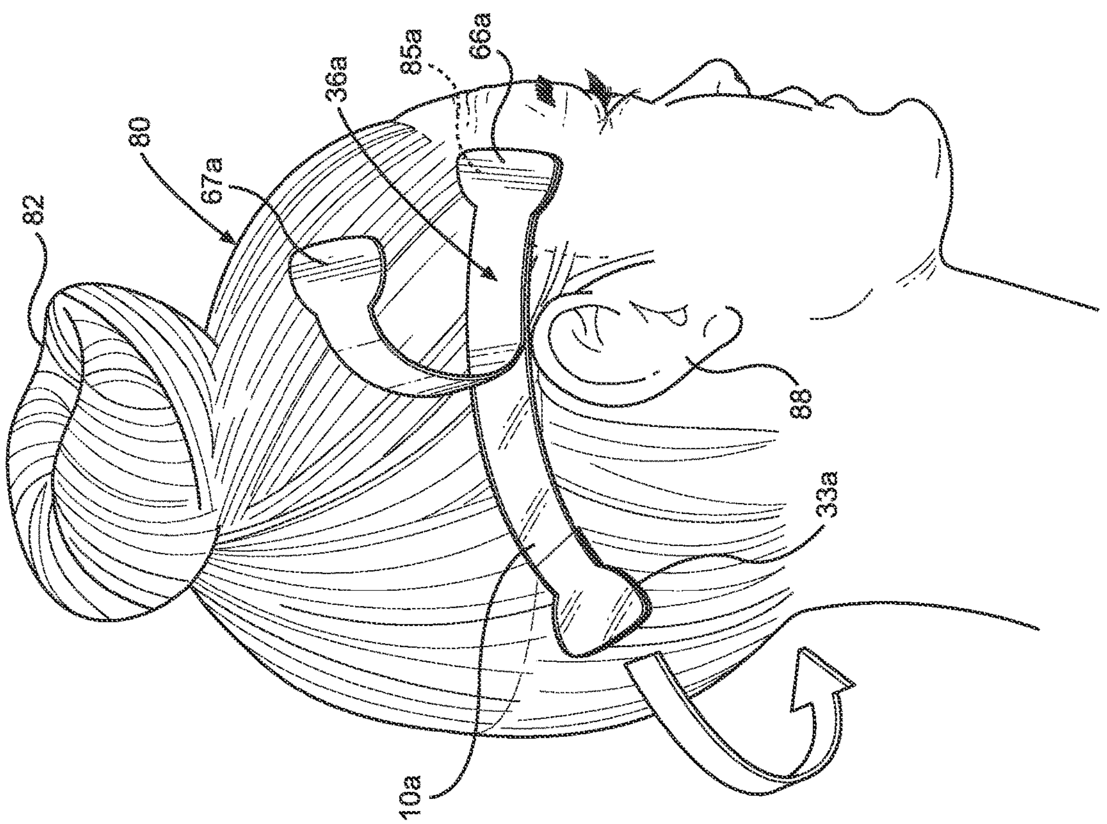
FIG. 6 illustrates an initial step associated with a method of non-invasively stretching the skin of a user's face with the device of FIGS. 1 and 2 in accordance with another preferred embodiment of the invention.

Certainly, the device can be positioned in various areas to pull and smooth different facial zones. As further illustration, reference will be made to FIG. 6-10 in describing a method of employing device 5 to stretch skin in other portions of a user's face. Starting with FIG. 6, the user's head 80 is again shown with hair pulled up at 82, first cover member 30 has already been peeled to expose first adhesive layer 22 and first end portion has been secured at a first attachment position **85*a* which is basically again shown to be located near a temple portion of the user and forward of a right ear 88 but rotated relative to the position shown in FIG. 3** so as to be angled further downward.

Figure 7:
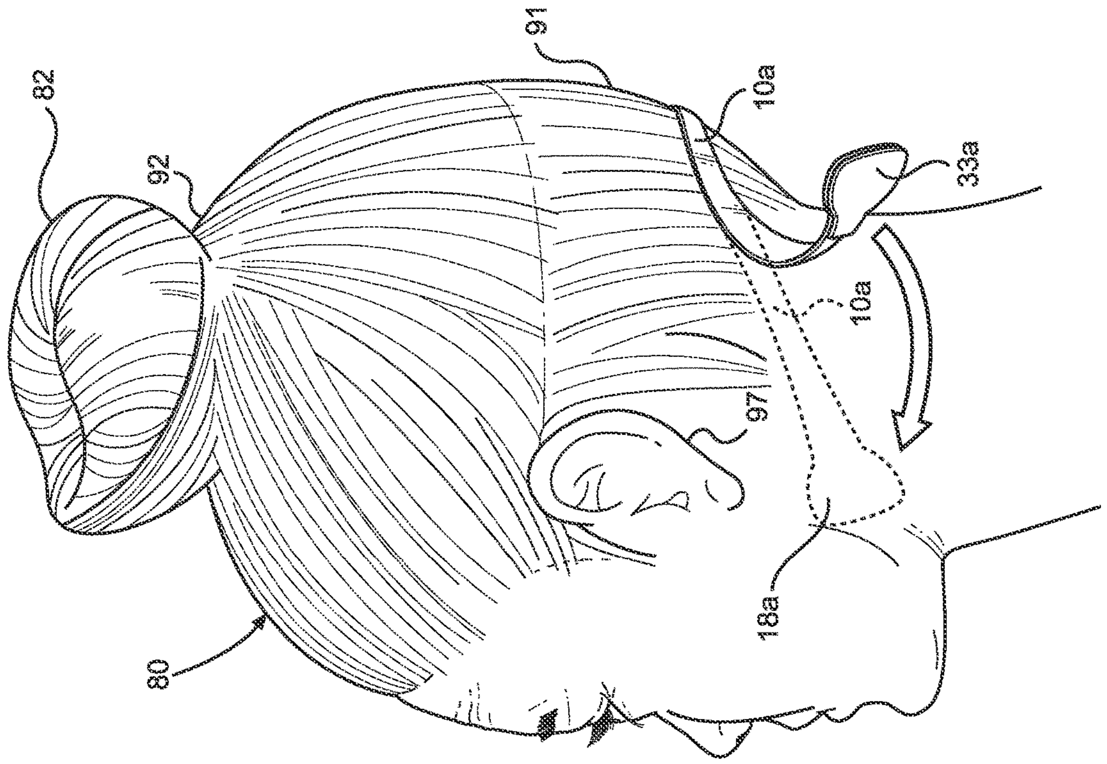
FIG. 7 shows latter stages in the method of FIG. 6.
Figure 8:
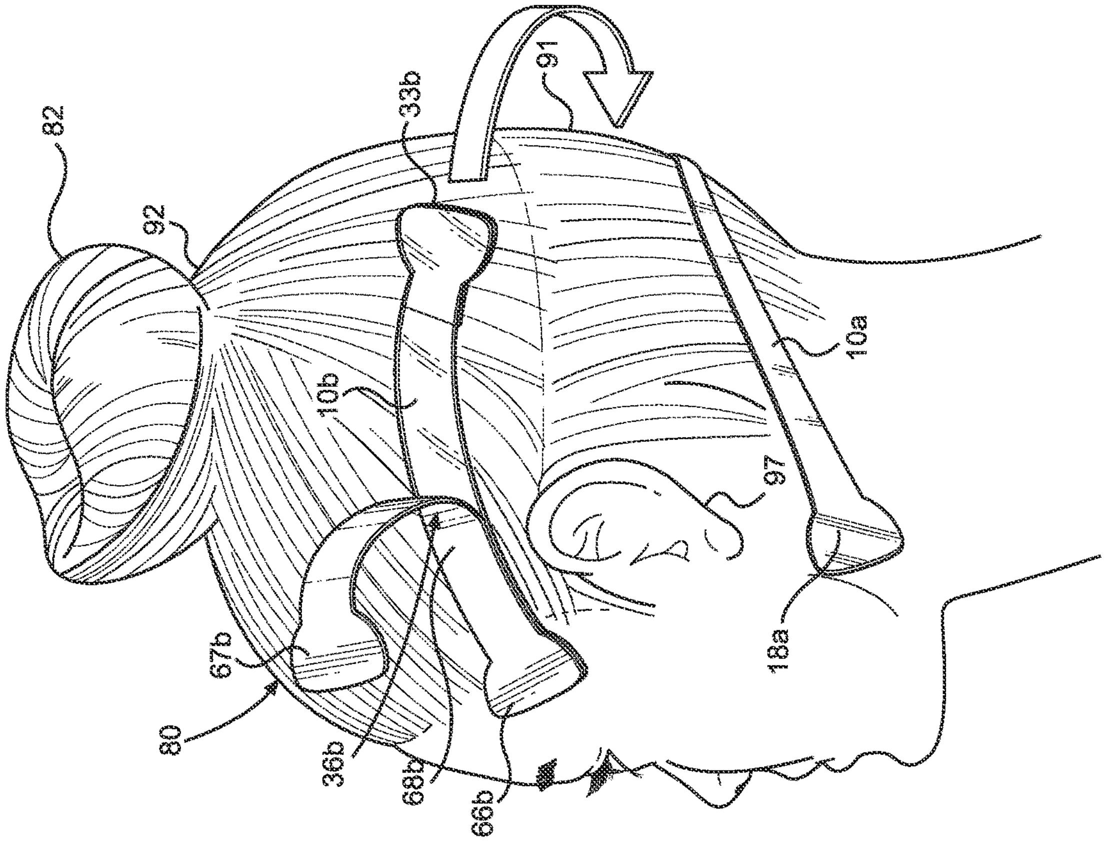
FIG. 8 illustrates the initial attachment of a secondary device applied in conjunction with the overall method of the embodiment of FIGS. 6 and 7.

In a next stage of the method, directly corresponding to the embodiment described above, cover strip **36*a* is completely removed, including first and second end portions 66*a* and 67*a*, to expose central body portion 10*a*. While pressing upon first attachment portion 15 and grasping second attachment portion 18*a* having second cover member 33*a*, device 5 is pulled so that central body portion 10*a* is stretched across the lower back 91 of head 80 as best shown in FIGS. 7 and 8. When fully extended, second attachment portion 18*a* will reach a second attachment position forward of left ear 97 and generally directly behind the user's cheekbone. Here, second cover member 33*a* is peeled to expose the second adhesive layer (not shown) and second attachment portion 18*a* is adhered as indicated with the use of the dotted lines in FIG. 7 and the solid lines in FIG. 8. Again, due to the elastic nature of device 5 (overall an elastic or resilient material that is skin-compatible) and particularly the elasticity of central body portion 10*a*, attaching device 5** in this manner will cause pulling and smoothing of another portion of the skin of the user's face.

Figure 9:
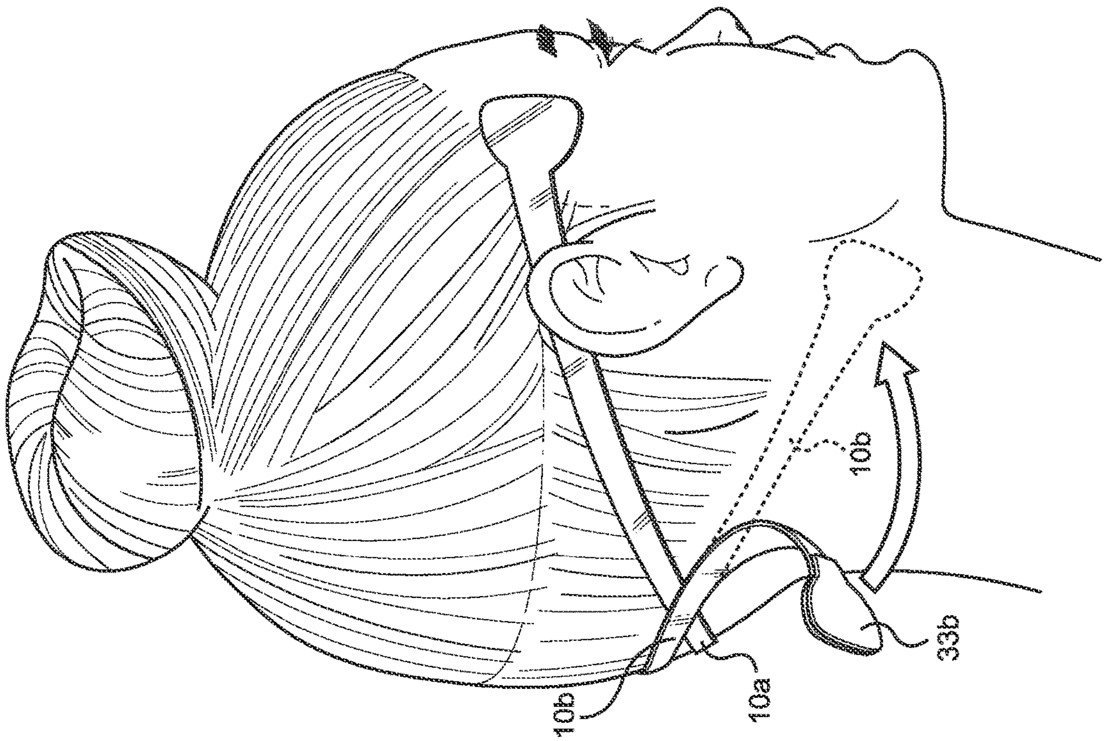
FIG. 9 illustrates latter stages associated with attaching the device depicted in FIG. 8.
Figure 10:
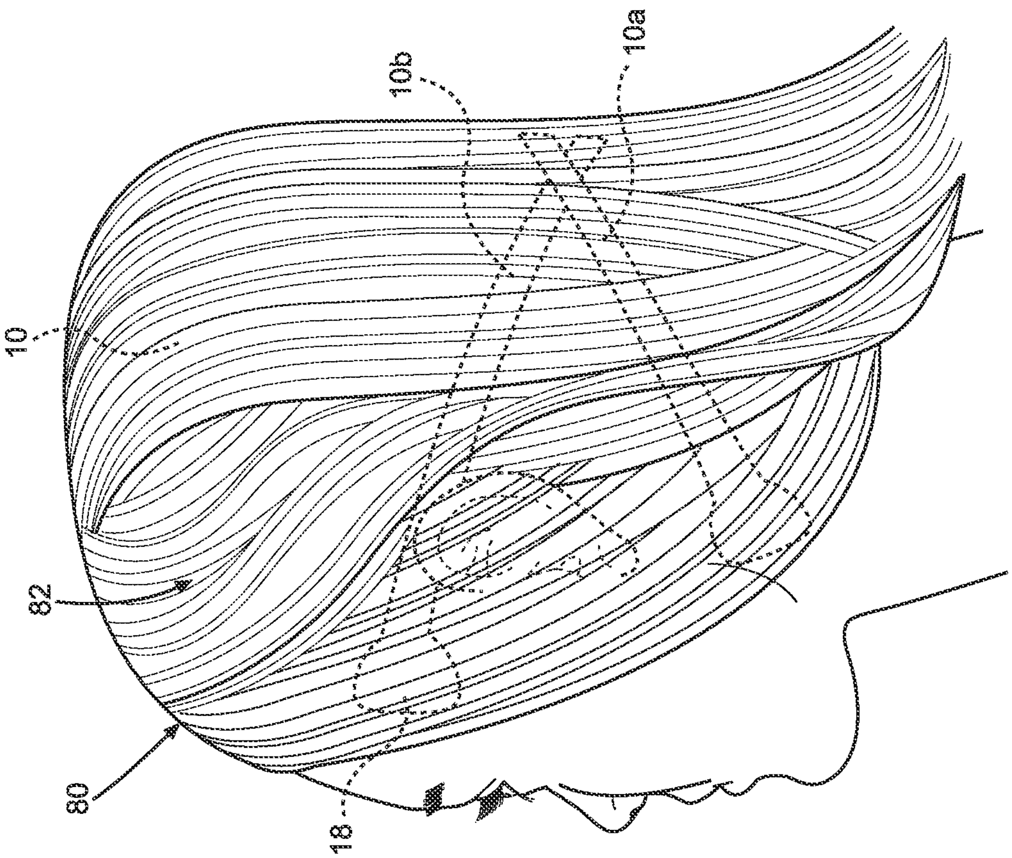
FIG. 10 shows a woman wearing the devices of the present invention beneath her hair to stretch skin portions of her face in accordance with the method of FIGS. 6-9.

With this embodiment, a pair of identically constructed devices 5 are preferably employed simultaneously. To this end, starting at FIG. 8, a first end portion of another device 5 is attached at or adjacent the left temple area, cover strip **36*b* is removed, including ends 66*b* and 67*b* along with connecting portion 68*b*, to exposed central body portion 10*b*. Device 5 is then stretched around the lower portion 91 of head 80 such that central body portion 10*b* crisscrosses with central body portion 10*a* as best shown in FIG. 9. Thereafter, second cover member 33*b* is removed and a final attachment is made below the right ear and, in this example, just behind the right cheekbone. At this point, the hair 82** which was originally pulled up at the top 92 of head 80 can be let down to cover devices 5 as shown in FIG. 10 to finalize the process.

Based on the above, it should be readily apparent that a single sized stretchable device of the invention can be used by varying sized individuals. Still, although described with reference to preferred embodiments of the invention, it should be readily understood that various changes and/or modifications can be made to the invention without departing from the spirit thereof. For instance, when two or more devices are simultaneously used, the devices need not criss-cross. Certainly, the length, width and thickness dimensions can greatly vary without departing from the invention. Preferably, the skin attached portions of the device are transparent so as to blend in with the user's skin if exposed. On the other hand, the device can come in various colors to match or even accessorize various skin and/or hair colors. In certain embodiments, apertures or holes can be provided to enhance stretchability and venting. Again, a preferred material for the invention is urethane, e.g., a transparent polyurethane. The polyurethane may be single coated to provide a fluid barrier that is breathable. The polyurethane may be supported by a polyethylene carrier. The tensile strength of the central body portion is preferably between 5-25 psi and, more preferably, between 10-15 psi. Advantageously, the central body portion is not completely elastic so the tension on the user's face can be selectively adjusted simply by the extent to which the central body portion is stretched, i.e., stretched beyond deformation, prior to securing the second attachment portion. The employed adhesive can also vary, while a high-grade medical adhesive, often employed with hospital bandages which can adhere even with the presence of moisture, such as from perspiration, is preferred. One preferred adhesive is a solvent based acrylic adhesive. The device can certainly be worn over the course of multiple hours, depending on the user's skin sensitivity and comfort. Overall, the invention provides a concealable, reliable, comfortable and economical alternative option to having a surgical face lift procedure taking less than five minutes to apply, with no downtime, no major cost, no surgery, or drugs.

The invention claimed is:

1. A device for stretching skin of a user's face comprising:

a flexible and stretchable central body portion which extends along a first axis, includes first and second end portions, and has first and second opposing sides;

a first attachment portion extending from the first end portion, the first attachment portion having first and second opposing side surfaces;

a second attachment portion extending from the second end portion of the central body portion, the second attachment portion having first and second opposing side surfaces;

a first adhesion layer provided on the first side surface of the first attachment portion;

a second adhesion layer provided on the first side surface of the second attachment portion;

a first peelable cover member removably provided on the first adhesion layer;

a second peelable cover member removably provided on the second adhesion layer, wherein the first attachment portion is configured to be attached to one side of a user's face through the first adhesion layer upon peeling away the first cover member, the central body portion is configured to be pulled and stretched around a head of the user while a width of the central body portion narrows, and the second attachment portion is configured to be attached to an opposing side of a user's face through the second adhesion layer upon peeling away the second cover member whereupon elasticity of the central body portion will cause pulling and smoothing of portions of the skin of the user's face; and a cover strip extending along the second side of the central body portion from the first end portion to the second end portion, preventing the central body portion from stretching until the cover strip is removed, wherein the cover strip has a first enlarged end, a second enlarged end, and an elongated connecting portion, which together define a shape substantially matching a shape of a combination of the first attachment portion, the second attachment portion, and the central body portion.

2. The device according to claim 1, wherein the second side of the central body portion is opposite the first side surfaces of each of the first and second attachment portions.

3. The device according to claim 2, wherein the cover strip further extends across the second side surfaces of each of the first and second attachment portions.

4. The device according to claim 1, wherein each of the first and second cover members includes a tab portion extending into the central body portion on a side of the central body portion opposite the cover strip.

5. The device according to claim 1, wherein the first and second attachment portions are enlarged in width relative to the central body portion.

6. The device according to claim 1, wherein each of the first and second attachment portions is configured for attachment forward of a respective ear of the user.

7. The device according to claim 1, wherein at least the central body portion is made of transparent urethane.

8. The device according to claim 1, wherein each of the first and second attachment portions has a width which is at least 1.5 times a width of the central body portion.

9. The device according to claim 8, wherein the first attachment portion, the central body portion and the second attachment portion constitute an integrally formed member, with each of the first and second attachment portions having a thickness which is equal to a thickness of the central body portion.

10. The device according to claim 8, wherein the device has an initial length, without stretching of the central body portion, of between 6-9 inches.

11. A method of stretching skin of a user's face with the device according to claim 1, comprising:

adhesively attaching the first side surface of the first attachment portion of the device to one side of the user's face;

pulling and stretching the central body portion of the device around a portion of the head of the user, during which the width of the central body portion narrows;

peeling the cover strip from the central body portion to enable the central body portion to stretch around the head of the user; and adhesively attaching the first side surface of the second attachment portion of the device to another side of the user's face, whereupon elasticity of the central body portion will cause pulling and smoothing of portions of the skin of the user's face.

12. The method of claim 11, further comprising:

peeling the first peelable cover member from the first side surface of the first attachment portion to expose an adhesive prior to adhesively attaching the first attachment portion to the user's face; and peeling the second peelable cover member from the first side surface of the second attachment portion to expose an adhesive prior to adhesively attaching the second attachment portion to the user's face.

13. The method of claim 11, wherein the cover strip is peeled from a side of the central body portion opposite the first side surfaces of the first and second attachment portions.

14. The method of claim 11, wherein each of the first and second attachment portions are adhesively attached to the user's face forward of and above a respective ear of the user.

15. The method of claim 11, further comprising: covering the central body portion with hair on the user's head.

16. The method of claim 11, further comprising: applying the device to the user with the first attachment portion, the central body portion and the second attachment portion constituting an integrally formed member, with each of the first and second attachment portions having a thickness which is equal to a thickness of the central body portion.

17. The method of claim 11, wherein the first attachment portion is adhesively attached to the user's face forward of and above a first ear on one side of the head of the user and the second attachment portion is adhesively attached to the user's face below an opposing, second ear of the user.

18. The method of claim 17, further comprising: attaching one end of a second device to the user's face forward of and above the opposing, second ear of the user, stretching a central body portion of the second device about the head of the user, and attaching another end of the second device to the user below the first ear of the user, with the second device crisscrossing the first device at a back portion of the head.

19. A device for stretching skin of a user comprising:

a flexible and stretchable central body portion which extends along a first axis, includes first and second end portions, and has first and second opposing sides;

a first attachment portion extending from the first end portion, the first attachment portion having first and second opposing side surfaces;

a second attachment portion extending from the second end portion of the central body portion, the second attachment portion having first and second opposing side surfaces;

a first adhesion layer provided on the first side surface of the first attachment portion;

a second adhesion layer provided on the first side surface of the second attachment portion;

a first peelable cover member removably provided on the first adhesion layer;

a second peelable cover member removably provided on the second adhesion layer, wherein the first attachment portion is configured to be attached to one side of a user through the first adhesion layer upon peeling away the first cover member, the central body portion is configured to be pulled and stretched while a width of the central body portion narrows, and the second attachment portion is configured to be attached to an opposing side of a user through the second adhesion layer upon peeling away the second cover member whereupon elasticity of the central body portion will cause pulling and smoothing of portions of the skin of the user; and a cover strip extending along the second side of the central body portion from the first end portion to the second end portion, preventing the central body portion from stretching until the cover strip is removed, wherein the cover strip has a first enlarged end, a second enlarged end, and an elongated connecting portion, which together define a shape substantially matching a shape of a combination of the first attachment portion, the second attachment portion, and the central body portion.

* * * * *